United States Patent [19]

Yang et al.

[11] Patent Number: 5,219,548
[45] Date of Patent: Jun. 15, 1993

[54] HIGH AFFINITY HALOGENATED-TAMOXIFEN DERIVATIVES AND USES THEREOF

[75] Inventors: David J. Yang, Sugarland; Sidney Wallace, Houston, both of Tex.

[73] Assignee: Board of Regents, The University of Texas System, Austin, Tex.

[21] Appl. No.: 589,928

[22] Filed: Oct. 1, 1990

[51] Int. Cl.$^5$ .................. A61K 49/02; A61K 43/00; A61K 31/135; C07C 91/06

[52] U.S. Cl. .................. 424/1.1; 564/324; 514/648; 514/651; 514/874

[58] Field of Search ............. 424/1.1; 514/648, 651, 514/874; 564/324

[56] References Cited

U.S. PATENT DOCUMENTS

| | | | |
|---|---|---|---|
| 3,288,806 | 7/1966 | DeWald | 564/324 X |
| 3,493,606 | 2/1970 | Richardson et al. | 514/874 X |
| 3,493,661 | 2/1970 | Holtkamp | 514/651 |
| 4,696,949 | 9/1987 | Toivola et al. | 514/648 |
| 4,806,685 | 2/1989 | Abraham et al. | 564/324 |
| 4,839,155 | 2/1989 | McCague | 424/1.1 |

FOREIGN PATENT DOCUMENTS

| | | |
|---|---|---|
| 0054168 | 1/1980 | European Pat. Off. |
| 0260066 | 9/1988 | European Pat. Off. |

OTHER PUBLICATIONS

Hanson et al. (1982), *Int. J. Nucl. Med. Biol.*, 9:105-107.
Loser et al. (1985), *Eur. J. Cancer Clin. Oncol.*, 21(8):985-990.
Yang et al. (Jun. 11, 1991), *The Society of Nuclear Medicine 38th Annual Meeting Cincinnati Convention Center*, No. 12071.
Tansey et al. (Jun. 11, 1991), *The Society of Nuclear Medicine 38th Annual Meeting Cincinnati Convention Center*, No. 32680.
Yang et al. (Jun. 30, 1992), *International Conference on Long-Term Antihormonal Therapy for Breast Cancer*.
Foster et al. (1986) *Anti-Cancer Drug Design*, 1:245-257.
Francesco et al. (1986) *Steroids*, 48(5-6):287-313.
International Search Report (1992).
Watanabe et al. (1989) *Journal of Chromatography*, 497:169-180.
D'Argy et al. (1989) *Chemical Abstracts*, 110(3):259, Abstract No. 20581h.
Kangus et al. (1989) *Chemical Abstracts*, 110(25):10, Abstract No. 224948t.
Hannu et al. (1990) *Chemical Abstracts*, 113(17):Abstract No. 144793k.
Pomper et al. (1988), *J. Med. Chem.*, 31:1360-1363.
Armstrong (1987), *Journal of Chromatography*, 414:492-196.

(List continued on next page.)

*Primary Examiner*—Robert L. Stoll
*Assistant Examiner*—John M. Covert
*Attorney, Agent, or Firm*—Arnold, White, Durkee

[57] ABSTRACT

Applicants describe the synthesis of fluorotamoxifen and iodotamoxifen analogs with the halogen atom positioned on the aliphatic chain of the tamoxifen molecule. The halogenated-tamoxifen derivatives possess superior binding affinities to estrogen receptors of pig uteri compared with tamoxifen. The fluorinated tamoxifens have potential use in imaging estrogen receptors by PET whereas the iodinated tamoxifens have potential use in imaging estrogen receptors by SPECT. Rapid and efficient methods of preparing fluorotamoxifen and iodotamoxifen derivatives with high specific activity are also disclosed. Fluorotamoxifen and iodotamoxifen derivatives may advantageously be used as anti-cancer therapeutic agents to halt estrogen-receptor positive tumors.

16 Claims, 1 Drawing Sheet

OTHER PUBLICATIONS

Lien et al. (1987), *Clin. Chem.* 33(9):1608–1614.
Yang et al. (1991), *Pharmaceutical Research,* 8(2):174–177.
Shani et al. (1979), *Cancer Treat Rep.* (USA), 63(7):Abstract No. 366.
Shani et al. (1985), *Med. Chem.* 28:1504–1511.
Mintun et al. (1988), *Radiology,* 169:45–48.
Foster et al. (1985), *J. Med. Chem.* 28(10):1491–1497.
Kangas et al. (1986), *Cancer Chemother Pharmacol* 17:109–113.
DeGregorio et al. (1989), *Cancer Chemother Pharmacol* 23:68–70.
DeGregorio et al. (1987), *Cancer Chemother Pharmacol* 20:316–381.
Kallio et al. (1986), *Cancer Chemother Pharmacol* 17:103–108.
Robertson et al. (1982), *J. Org. Chem.* 47:2387–2393.
Katzenellenbogen et al. (1984), *Cancer Research* 44:112–119.
Kuroda, et al. (1985), *J. Med. Chem* 28:1497–1503.
Ram et al. (1989), *Journal of Labelled Compounds and Radiopharmaceuticals,* 27(6):661–668.

Fig. 1

HIGH AFFINITY HALOGENATED-TAMOXIFEN DERIVATIVES AND USES THEREOF

BACKGROUND OF THE INVENTION

1. Field of the Invention

The present invention relates to the field of tamoxifen derivatives. In that novel tamoxifen derivatives are described wherein the alkyl chain of the molecule is substituted with fluorine or iodine, the present invention also relates to methods of synthesizing the novel fluoro- and iodo-tamoxifen analogs and derivatives. In that the described tamoxifen derivatives have high affinity for binding estrogen receptors and may be labeled with detectable "tagging" molecules, rendering highly visible labeled estrogen receptors through position emission topography (PET) and single proton emission tomography (SPECT), the present invention also relates to the field of Positron Emission Topography and single photon Emission Tomography reagents and radiopharmaceuticals. The haloginated tamoxifen derivatives of the present invention are advantageously used in the imaging of estrogen receptors, for example, in breast, ovarian, uterine and brain tissue.

The present invention also relates to the field of anti-cancer therapeutic agents, particularly to methods of breast tumor therapy and diagnosis, in that the described high estrogen receptor binding affinity iodo- and fluoro- tamoxifen analogues may be advantageously used in the therapy and diagnosis of estrogen-receptor positive breast cancers.

2. Background of the Invention

Endocrine therapy is one of the oldest nonsurgical methods for treatment of breast carcinoma, and is still considered standard for certain subsets of patients, typically postmenopausal women with primary tumors and tumors having high estrogen levels.[1-3] The synthesis of F-18 fluoroestradiol for application in diagnosing breast tumors in humans has recently been described.[4] Observation of significant changes in the binding of estrogen receptors in breast tumors were reported using PET. However, technical difficulties associated with estrogen receptor saturation in patients receiving tamoxifen, or other estrogen receptor antagonist, has been observed to decrease the sensitivity and accuracy of using an estrogen-based receptor tag in diagnosing and monitoring the progress of tumors in patients receiving such treatments.

Tamoxifen (I), a potent non-steroidal anti-estrogen, has been widely used in the treatment of human breast tumors. Tamoxifen has few side effects when compared with other hormonal treatments. Tamoxifen is cytostatic (i.e, it prevents/inhibits cell growth), and exerts competitive inhibitory activity at the receptor level with estrogen. More specifically, the cytostatic activity of tamoxifen is described from its action to bind to cytoplasmic estrogen receptors and is translocated to cell nuclei, where cell proliferation is prevented.[1-3] Thus, tamoxifen is often administered as an anti-cancer agent.[6] For example, Foster et al. describes the effect of various tamoxifen hydroxyderivatives on the growth of MCF-7 breast cancer cell line (Id.) in its native form. However, highly active in vitro hydroxy tamoxifen derivatives were found to be less active than tamoxifen in vivo against a DMBA-induced ER-positive tumor in rats and only slightly more active against a hormone dependent mammary tumor in mice.

Tamoxifen has a relatively low binding affinity for the estrogen receptor (ER). Attempts have therefore been made to synthesize tamoxifen derivatives having improved ER binding affinity to enhance to action as an anti-cancer therapeutic agent. A variety of these tamoxifen derivatives have been described in the literature. Structural modifications have been made at virtually every site on the three aromatic rings of the tamoxifen molecule. The structure of tamoxifen is demonstrated as:

For example, 4-hydroxy tamoxifen derivative in which X=—OH, was shown to be a potent anti-estrogen, but proved in vivo to be less effective than tamoxifen, owing to rapid glucuronidation of the hydroxyl group followed by excretion.

Other tamoxifen derivatives having a 4-position substitution of the phenyl ring, in which X is methoxy, methyl, fluoro or chloro, have also been proposed and evaluated.[15] K. E. Allen et al. (1980) conducted studies wherein the 4- methyl, chloro- and fluoro-derivatives were evaluated and found to have approximately equiactivty for estrogen receptor affinity compared to tamoxifen in vitro. However, in vitro uterine weight tests indicated that these derivatives had lower antiestrogenic activity than tamoxifen, while other tests indicated that the activity of the 4- methoxy derivative was about the same as tamoxifen.

A 4- iodo substitution of the phenyl ring as a tamoxifen derivative (formula 2: X=iodo) has recently been found to have greater potency than tamoxifen in relation to detecting estrogen receptor-positive breast cancer.[13] Other 3- and 4- iodo and -bromo-phenyl ring substituted tamoxifen derivatives- have also been described.[13] For example, the McCaque et al. patent (U.S. Pat. No. 4,839,155), described the preparation of a halogenated tamoxifen. The halogen atom (i.e., I or Br) was substituted at one of the phenyl rings of the tamoxifen structure.

However, derivatives of tamoxifen wherein sites other than those on the phenyl groups of the molecule are substituted have not been proposed in the art. Such a molecule would be desirable, as it would leave the major portion of the molecule unchanged and free to bind with the "target" molecule or tissue cells. Additionally, to further enhance tissue targeting specificity, the tamoxifen molecule would preferably be coupled with a targeting molecule such as a microparticle. Such a tamoxifen derivative has not as yet been developed, and would represent a tremendous improvement in the quality of imaging techniques currently available, as well as improve the quality and accuracy of PET and SPECT scans.

Other alternative compounds proposed as a possible steroid radiopharmaceuticals useful in the imaging of steroid receptors include labeled progesterone and estrogen derivatives. For example, Pomper et al. described a ligand for the progesterone receptor.[16] This aliphatic fluorination of FENP (21-[$^{18}$F] fluoro-16 α-ethyl-19- nor progesterone) is described as demonstrating a high specific uterine target tissue uptake.[16] This ligand for the progesterone receptor is labeled with the position-emitting radionucleotide fluorine-18 (t ½ = 110 min). Estrogen-based imaging agents described in the literature include radionucleotides of iodine[20], fluorine[19], and bromine[21]. By way of example, a specific fluorine described in the 16 α-[$^{18}$F] fluorolstradiol ligand.[17]

The preparation of 16 α-[$^{18}$F] fluoroestrogens and their selective uptake by estrogen target tissues in rats has been described by Kiesewetter et al.[19]. Additionally, significant changes in the binding of estrogen receptors in breast tumor were reported with the use of [$^{18}$F] fluoroestradiol using PET.[4] However, the radioisotope $^{18}$F has a very short half life, and therefore techniques and molecules which employ this radioisotope must be rapid, and preferably more rapid than currently employed molecule labeling techniques allow.

Additionally, the use of an estrogen-based agent in response to hormone therapy with estrogen receptor positivity may not closely correlate actual physiological response to the hormonal therapy. A progestin-based imaging agent for breast tumors might be preferred over an estrogen-based agent because response to hormonal therapy is more significantly correlated with progesterone receptor positivity than with estrogen receptor positivity.[17] It has further been reported that estrogen receptor positive tumors in patients on hormonal therapy (e.g. tamoxifen) could not be imaged with an estrogen, as the circulating levels of tamoxifen and its metabolites are sufficiently high to fully occupy the estrogen receptor.[18]

While the tamoxifen derivatives described in the literature have demonstrated some increase in estrogen receptor binding affinity, they do not demonstrate sufficient specific radioactivity due to the fluorine modification of those molecules at sites on the phenolic rings. Thus, the enhanced estrogen receptor binding affinity is achieved at the expense of a loss in specific activity. The fluorine-18 [$^{18}$F] ion radioisotope reportedly has a low effective dose equivalency and a short half-life (+ ½ = 110 min). For these reasons, methods which require [$^{18}$F] in labeling the tamoxifen molecule must be rapid (i.e. within a 2 hour reaction time) to avoid a loss in activity of the label.

Tamoxifen derivatives substituted at various phenolic sites of the tamoxifen structure may block the active hydroxy metabolite formation. This may decrease the tamoxifen analogs potency and receptor binding affinity. On the other hand, an elimination reaction may occur due to competition with active metabloite formation on the phenyl ring. A tamoxifen derivative which therefore was instead substituted at other sites on the molecule would advantageously provide a molecule with an endhanced in vivo stability and estrogen receptor binding capacity than currently available derivatives and analogs.

SUMMARY OF THE INVENTION

The present invention provides novel iodo- and fluoro-tamoxifen derivatives found to have surprisingly and unexpectedly enhanced binding affinity for estrogen receptors. The particular chemistry of the claimed tamoxifen derivatives advantageously provides a rapid and simple method for the fluorine and iodine labeling of the tamoxifen molecule at a non-aromatic carbon of the tamoxifen alkyl chain. The claimed no-carrier-added radiolabeled tamoxifen derivatives are unlike any other labeled tamoxifen derivative described in the literature[13], and posses an enhanced binding affinity for estrogen receptors while retaining high specific activity. This more enhanced binding affinity of the described derivatives is advantageously employed in a diagnostic test to identify and treat estrogen receptor-positive (hormone dependent) breast tumors (i.e., cancers). Additionally, the derivatives may also be advantageously used to predict the efficiency of tamoxifen therapy for breast tumors.

Applicants' fluorine-substituted tamoxifen derivatives include a fluorine atom strategically placed on the aliphatic chain of the tamoxifen molecule. Thus modified, the molecule is imparted enhanced estrogen receptor binding affinity compared to native tamoxifen. Additionally, the placement of the fluorine or iodine molecule at the aliphatic side chain, rather than on the aromatic portions of the tamoxifen structure, preserves the major portion of the tamoxifen for binding with a minimum of alteration of the tamoxifen structure. Also, substitution of the N,N-dimethyl of tamoxifen with N,N-diethyl is demonstrated by Applicants to increase binding of the tamoxifen derivative to estrogen receptors up to 30- fold, with the binding increased in all cases at least by 4- fold.

Radiolabelling of tamoxifen derivative with [$^{18}$F] or [$^{131}$I] provides a molecule with both high specific radioactivity and high estrogen receptor binding affinity.

The described distinguishing structural features of the claimed fluoro- and iodo- substituted tamoxifen derivatives from native tamoxifen establish in part the superior nature of the claimed derivatives over those N,N-dimethyl tamoxifen derivatives described by Foster et al.[6] The claimed derivatives also feature the specific substitution of tamoxifen with a fluorine or an iodine molecule at the alkyl chain of the structure, in contrast to the substituted tamoxifen structure described in Foster et al.[6] Thus, the synthesis and chemical structure of the claimed derivatives are distinct from those derivatives discussed in the literature, including the phenolic ring substituted tamoxifen derivtive described by McCague in U.S. Pat. No. 4,839,155.

Most generally, the tamoxifen derivatives of the claimed invention comprise the following structure:

(1)

wherein $R_1$ is fluorine, iodine, fluoromethyl, iodomethyl, hydroxy or hydroxymethyl; $R_2$ is methyl or ethyl; $R_3$ is methyl or ethyl, and wherein $R_2$ is not methyl when $R_3$ is methyl. In a most preferred embodiment of the described tamoxifen derivatives, $R_2$ and $R_3$ are most particularly defined as ethyl. In still another embodiment, $R_2$ is methyl and $R_3$ is ethyl. In particular embodiments of the invention, $R_1$ is fluoromethyl and $R_2$ and $R_3$ are ethyl. In still another embodiment, $R_1$ is preferably iodomethyl and $R_2$ and $R_3$ are ethyl.

In a second most particularly preferred embodiment, the tamoxifen derivatives included within the scope of the invention are radiolabeled, and comprise:

(2)

wherein X is 18-F, 131-I, [18-F] fluoromethyl, or [131-I] iodomethyl; $R_2$ is methyl or ethyl, and wherein $R_3$ is methyl or ethyl. Most preferably, $R_2$ is not methyl when $R_3$ is methyl. In a particularly preferred embodiment of this particular tamoxifen derivative, $R_1$ is [18-F] fluoromethyl, $R_2$ is ethyl, and $R_3$ is ethyl. The three phenyl rings of the tamoxifen structure are unsubstituted phenyl rings. In still another particularly preferred embodiment, X is [131-I] iodomethyl, $R_2$ is ethyl and $R_3$ is ethyl.

The fluoromethyl tamoxifen derivatives herein disclosed demonstrate a synergistically enhanced binding affinity for estrogen receptors over that binding affinity of native taxoxifen, having a a 30-fold (trans) and 6-fold (cis) enhancement of estrogen receptor binding affinity. For iodomethyl tamoxifen analogs, the trans isomer has 15-fold and the cis-isomer has a 10-fold enhancement of estrogen receptor binding affinity. Particular of the tamoxifen derivatives exhibit at least a 4- fold increase in estrogen receptor binding affinity compared to native tamoxifen.

Because of the enhanced estrogen receptor binding affinity demonstrated by the described tamoxifen derivatives and analogues, Applicants provide an efficient and specific reagent which is useful in the imaging of estrogen receptors. In such an embodiment, the tamoxifen derivative includes a radiolabel, most preferably an $^{18}F$ or $^{131}I$ radiolabeled tamoxifen derivative. In a most particularly preferred embodiment of such an imaging reagent, the "tag" is an $^{18}F$ or $^{131}I$ radionucleotide located at the alkyl side chain of a halogen-substituted tamoxifen molecule. Most preferably, the alkyl side chain comprises a carbon chain of at least two carbons. Methods of performing the described radiosynthesis of the disclosed [18-F] fluoromethyl-substituted derivatives and [131-I] iodomethyl substituted derivatives of tamoxifen are also provided herein.

The presently disclosed tamoxifen derivatives provide an improved method by which estrogen receptors may be imaged through a PET or a SPECT radioimaging protocol. In that the halogen-substituted derivatives of tamoxifen disclosed herein have enhanced estrogen receptor binding affinity, an estrogen receptor binding agent with enhanced receptor binding affinity comprising such halogen-substituted tamoxifen derivatives is provided. Most particularly, the halogen to be substituted is fluorine or iodine.

Additionally, in order to even further enhance the tissue-targeting of the derivatives to those tissues known to be rich in estrogen receptors, Applicants propose to couple the described radiolabeled, fluorine or iodine alkyl chain substituted tamoxifen derivatives with a microparticle. Such is accomplished by reacting the halogenated-tamoxifen with a polymer in the presence of a coupling reagent (e.g., dicyclohexylcarbodiimide). The coupling of the tamoxifen derivative with the microparticle is expected to enhance the tissue targeting of the molecule. The payload (e.g., chemotherapeutic agent) can then be released from microparticles and used to kill tumors.

While any fluorotamoxifen and iodotamoxifen derivative, wherein the halogen-substitution is located at the tamoxifen alkyl side chain (a non-aromatic carbon of the tamoxifen molecule) would be capable of providing the claimed derivative imaging agent with enhanced estrogen receptor binding affinity, those fluoro- tamoxifen derivatives most preferred in the present invention include N-N-diethylfluorotamoxifen and N,N-diethylfluoromethyltamoxifen. The most preferred iodotamoxifen derivatives of the described estrogen receptor radiopharmaceutical agents is iodomethyltamoxifen labeled with 131-I.

One object of the present invention is to provide an estrogen receptor imaging reagent suitable for use in positron emission tomography which has high affinity for the estrogen receptor and high specific activity. Another object of the invention is to provide an imaging reagent which, as a result of the foregoing characteristics, has superior target tissue selectivity in vivo. Another object of the present invention is to provide a method whereby the efficiency of tamoxifen therapy for breast tumors may be monitored.

A further object of the present invention is to achieve a halogen-substituted tamoxifen derivative which has both higher estrogen receptor binding affinity, and a high specific activity. More specifically, an object of the present invention is to provide a fluoro- or an iodotamoxifen derivative with high specific activity which may be rapidly and easily labeled with $^{18}F$ or $^{131}I$ at the aliphatic chain of the tamoxifen structure.

By providing a halogen at the aliphatic chain of the tamoxifen molecule, an object of the present invention is to preserve the native structure of the molecule, leaving most of the molecule available for binding receptors.

Because of the site specificity of the [$^{18}F$] and [$^{131}I$] tamoxifen labeling of the aliphatic chain of the molecule provided by the present invention, an additional object of the invention is to provide a simple and inexpensive method for radiosynthesizing these derivatives.

Additionally, since current methods for directing the substitution of tamoxifen at the aliphatic chain involve multiple and time consuming steps, the formulation of a more efficient and rapid method for preparing iodo- and fluorine- alkyl chain substituted tamoxifen derivatives with $^{18}F$ and $^{131}I$ would represent a significant and valuable advance in the use of this molecule as radiopharmaceuticals. The $^{18}F$ radionuclide is known to have an extremely short half life of only about 2 hours. Time is, therefore, of the essence in processing these molecules.

An additional object of the present invention is to provide iodo- and fluoro- tamoxifen derivatives which have superior estrogen receptor binding affinities compared to the described tamoxifen and progestin derivatives in the literature. In regard to the $IC_{50}$ values, it should be considered that different species (e.g., pig, rat, dog, rabbit) will have different $IC_{50}$ values (for the same compound). However, the Ki as calculated with a standard compound should remain the same. Therefore, to report data, one must include a standard sample (e.g., tamoxifen, estradiol, diethylstilbestrol) and compare the relative value to a standard sample. $IC_{50}$ values, therefore, between species cannot be readily compared. Relative binding affinities are more easily comparable.

Another object of the present invention is to provide a more stable in vivo reagent. An advantage of adding halogen atoms to the tamoxifen aklyl chain is that it provides a greater in vivo stability to the molecule. The active metabolite of tamoxifen is formed at the 4-position of the aromatic ring. Thus, if halogen is placed on the phenyl ring, it will compete with the active metabolite formation and the elimination reaction described herein may then occur, making derivatives substituted on the phenyl ring less stable in vivo.

In that the described molecules have enhanced binding affinity for estrogen receptors, an additional object of the invention is to provide an effective anti-cancer therapeutic agent for reducing estrogen-receptor positive breast, ovarian, uterine and estrogen receptor-rich tissues of the brain.

An ultimate object of the present invention is to provide a non-estrogen based radiopharmaceutical agent useful in PET which has both high affinity for the estrogen receptor and high specific activity, and hence high target tissue selectivity. The tissue selectivity is sought to be further enhanced by coupling this highly selective radiopharmaceutical with a targeting agent, for example, with microparticles.

The following numerical designation of particular tamoxifen compounds is employed throughout the Specification:

Compound I—Tamoxifen
Compound II—N,N-diethyl hydroxytamoxifen
Compound III—Hydroxymethyl N,N-diethyl tamoxifen
Compound IV—N,N-diethyl fluorotamoxifen
Compound V—Hydroxytamoxifen
Compound VI—N,N-diethyl Fluoromethyltamoxifen
Compound VII—N,N-diethyl tamoxifen
Compound VIII—N,N-diethyl-O-tosyl-tamoxifen
Compound IX—N,N-dimethyl-O-tosyl methyl tamoxifen
Compound X—N,N-diethyl iodomethyltamoxifen The following abbreviations are included throughout the body of the Specification:

$IC_{50}$=the concentration of test compounds that decreases 50% of specific raioligand binding in receptor assay or 50% of cell viability in MCF-7 cell growth assay.
PET=positron emission topography
$K_d$=dissociation constant determined from a saturation estrogen receptor assay and a Scatchard analysis.
ER=estrogen receptor
$K_i$=inhibition constant determined using the equation $$K_i = \frac{IC_{50}}{1 + [^3H] \text{ estradiol}/Kd}$$

RBA=relative binding affinity, the relative concentration of estradiol and tamoxifen or its derivatives required to achieve 50% inhibition of $[^3H]$-$E_2$ binding.
RP=relative potency

DETAILED DESCRIPTION OF THE PREFERRED EMBODIMENTS

The present invention disclose a tamoxifen derivative having surprisingly enhanced estrogen receptor binding affinity. The particular derivatives described herein are substituted with a halogen molecule and comprise the group of compounds described herein as fluorotamoxifen (FTX) and iodotamoxifen (ITX) derivatives. The fluorotamoxifen and iodotamoxifen derivatives have been radiolabeled to provide reagents having high specific activity in estrogen receptor mapping.

Unlabeled forms of the described fluorotamoxifen derivatives were prepared from hydroxytamoxifen via diethylaminosulfur trifluoride reaction at a 47% product yield. The binding affinity of these particularly synthesized fluorotamoxifen derivatives to cytosol estrogen receptors of pig uteri in vitro was higher ($K_i$ is 500 nM; trans-compound VI) than that binding affinity observed between estrogen receptors and native tamoxifen ($K_i$ is 1500 nM).

Unlabeled forms of iodomethyltamoxifen were prepared from tosyl analogs of tamoxifen by reacting with sodium iodide. The binding affinity of iodotamoxifen was 10–18 fold higher than tamoxifen.

Radiosynthesis with fluorine-18 was performed on tosyl tamoxifen analogs to produce radiolabeled fluorotamoxifen molecules having the described high specific activity (2–4 Ci/μmol) and a radiochemical yield of 60%. Radiochemical purity was >99%. Radiosynthesis of $^{131}I$-labeled analogs (Compound X) of tamoxifen was performed by reacting tosyl analogs of tamoxifen with NaI. The radiochemical yield was 60%.

Clomiphene, estradiol, and tamoxifen were obtained from Sigma Chemical Company (St. Louis, MO). Flash chromatography was used by the procedure of Still et al.[7] Silica gel Sep-Paks from Waters Associates (Milford, MA) were used for purifications. Thin-layer chromatographic (TLC) analysis was performed on Whatman K6F silica gel-packed plates (250 μm) (Anspec, Mich.). $[^3H]$estradiol (specific activity 160 Ci/mmol) for receptor binding was purchased from Amersham (Arlington Heights, Ill.). The no-carrier-added Na$^{131}I$ was purchased from Syncore. High pressure liquid chromatography (HPLC) was carried out on a LDC system, consisting of two LDC ConstaMetric Pumps, a Rheodyne injector and a Spectra Physics model SP8450 variable UV/Vis detector.

Melting points were determined on a Meltemp melting point apparatus and are uncorrected. $^1$HNMR spectra were obtained from a GE 300 MHz instrument, and mass spectral data were obtained by direct probe analysis (Finnigan MAT INCOS-50) at The University of Texas Health Science Center, Houston, Texas. Elemental analyses were performed by Galbraith Laboratories, Inc., Knoxville, Tenn.

Figure 1:
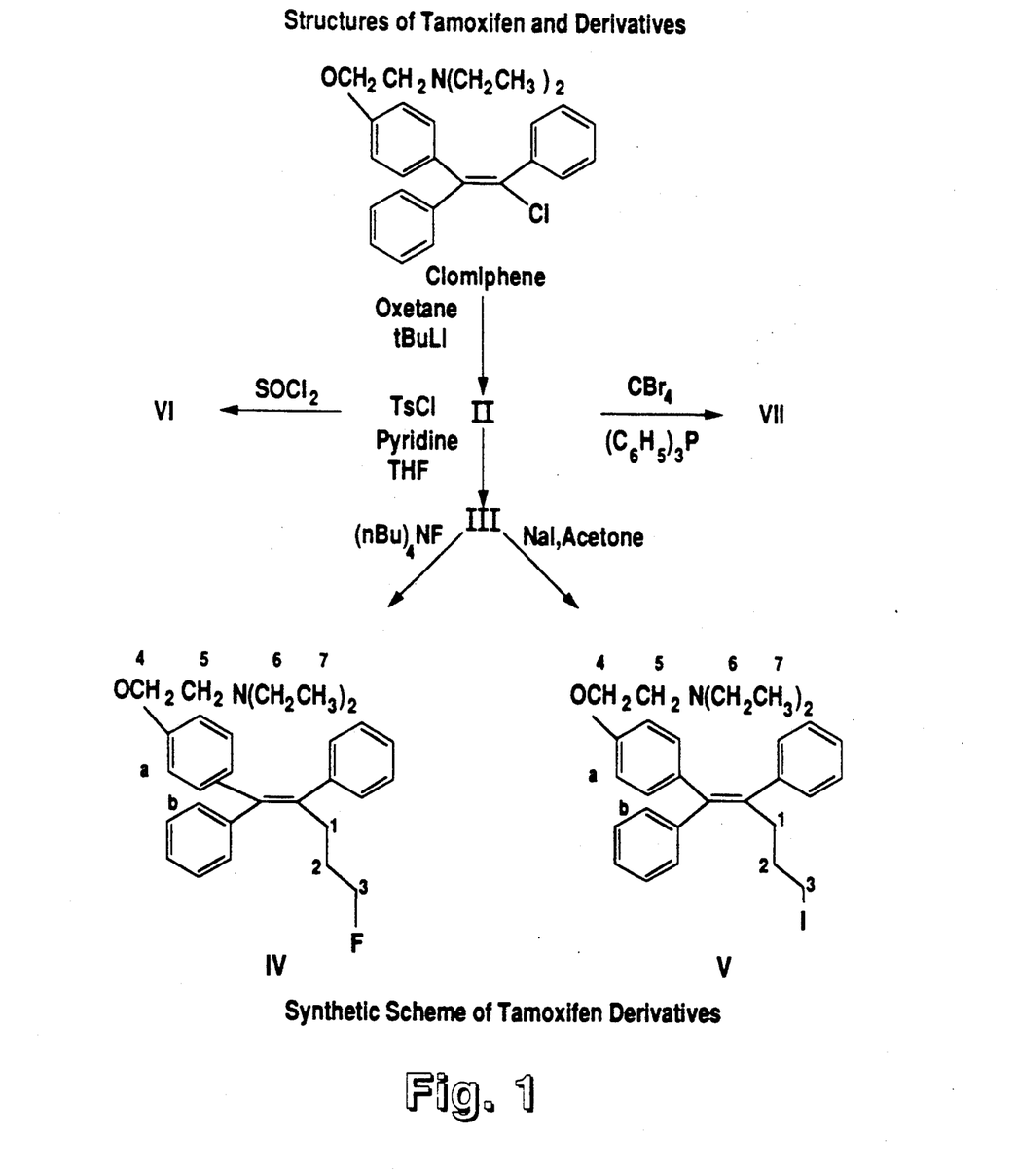
FIG. 1—Synthesis of Tamoxifen Derivatives.

Improved and more efficient methods for the synthesis of N,N-diethylfluorotamoxifen, fluoromethyl-N,N-diethyltamoxifen and iodomethyl-N,N-diethyltamoxifen is also part of the disclosed invention. Specifically, synthesis has been simplified from an at least ten (10) step procedure to a more rapid and simple three-step procedure (FIG. 1). The N,N-diethylfluoro (Compound IV) and the N,N-diethylfluoromethyl (Compound VI) and N,N-diethyliodomethyl (Compound X) analogs of tamoxifen were prepared for preliminary evaluation according to these improved protocols. N,N-Diethylfluoro (IV), N,N-diethylfluoromethyl (VI) and N,N-diethyliodomethyl (X) analogues of tamoxifen were prepared from the corresponding hydroxy analogues of tamoxifen via tosyl analogues by displacement with either fluoride or sodium iodide.

The cis- and trans-isomers of the desired products were separated by passing the reaction mixture through a silica gel-packed column and eluting with ether/petroleum ether/triethylamine (1:1:0.1). The $^1$HNMR chemical shift signals for cis- and trans-isomers were assigned based on published information.[8,11]

It was ascertained that the tosyl group on N,N-diethyl-O-tosyltamoxifen could be displaced by nucleophilic fluoride substitution reaction with a milder condition (e.g. kriptofix-222 and KF). Using this procedure, the fluoro- analogue of tamoxifen (IV) was prepared in 40% yield from the corresponding tosyl derivative of hydroxytamoxifen. However, elimination occurred to form the butadiene by-product in the presence of the stronger base (e.g. tetrabutylammoniuahydroxide). The formation of the butadiene by-product is due to an elimination reaction on the tosyl analogue.

Synthesis of Halogen-methyl Analogs of Tamoxifen

| COMPOUND | R' |
|---|---|
| VI | F |
| X | I |

Increasing the side chain by one carbon results in the synthesis of cis fluoromethyl-N,N-diethyltamoxifen (VI), which is more stable toward tosyl elimination. The yield for compound VI was 60%. Compound VI showed a 6-fold (cis) and 30-fold (trans) higher affinity for the estradiol binding site than native tamoxifen. The yield for Compound X was 50% (trans) and 70% (cis). Compound X showed a 10-fold (cis) and 15-fold (trans) higher ER affinity than tamoxifen. Receptor binding affinity of fluorotamoxifen with a flurorine atom placed on the phenyl ring of tamoxifen and iodotamoxifen with an iodine atom placed on the phenyl ring of tamoxifen has been reported.[22,23] However, the reaction preparation used for fluorotamoxifen can only preserve low specificity for $^{18}$F-labeled tamoxifen, which is not practical for estrogen-receptor studies using PET.

The iodine atom placed at the position 2 next to the phenoxy ring gave a poor estogen receptor binding. The iodine atom placed on 4-position of the aromatic ring gave a good receptor binding [13], yet it may be unstable in vivo due to an elimination reaction by its active hydroxy metabolite.

The following Examples are presented only to describe preferred embodiments and utilities of the present invention, and to satisfy best mode requirements. The examples are not meant to limit the scope of the present invention unless specifically indicated otherwise in the claims appe ed hereto.

EXAMPLE 1

Synthesis of Trans-Fluorotamoxifen (Compound VII)

Hydroxytamoxifen (trans) (V) (8) (330 mg, 0.85 mmol) was dissolved in methylene chloride (20 ml), cooled to −40° C. and then treated with triethylamine (200 μl) added. Diethylaminosulfur trifluoride (250 μl, 1.89 mmol) was added and the reaction mixture was stirred for 1 hour at −40° C. according to our previous published method.[9] The reaction mixture was then washed with water and the methylene chloride layer evaporated to dryness. The reaction mixture was chromatographed on a silica gel column using 1:1:0.1 hexane/ethylacetate/triethylamine as eluant to yield 145 mg (43.7%) of VII:$R_f$ 0.40 (1:1:0.1 ether/petroleum ether/triethylamine); $^1$HNMR (CDCl$_3$) δ 2.29 (S, 6, NMe$_2$) 2.66 (t, J=5.6Hz, 2, OCH$_2$CH$_2$N), 2.87 (dt, J=21.2 Hz, 6.3Hz, 2, CH$_2$CH$_2$F), 3.93 (t, J=5.5 Hz, 2, OCH$_2$CH$_2$N), 4.34 (dt, J=47.2 Hz, 6.3Hz, 2, CH$_2$F), 6.56 (d, J=8.5Hz, 2, ArH 3,5 to OCH$_2$), 6.77 (d, J=8.3 Hz, 2, ArH 2,6 to OCH$_2$), 7.12–7.35 (m, 10, ArH); m/z 389 (12, M+), 342 (30, +CH$_2$-CH$_2$-F).

EXAMPLE 2

Synthesis of N,N-Diethylhydroxytamoxifen (Compound II)

Clomiphene (6.06 q, 14.9 mmol) was dissolved in tetrahydrofuran (100 ml) and cooled to −40° C. t-Butyl lithium (1 M in pentane, 24 mmol) was added slowly. After 5 minutes, ethylene oxide (14.6 ml, 290 mmol) was added, and the reaction mixture was stirred for 6 hours, poured into water and extracted with ether. The ether layer was evaporated and chromatographed on a silica gel column using 1:1:0.1 ether/petroleum ether/triethylamine as eluant to yield trans product (1.96 g, 27.1%, oil): and cis product (1.56 g, 21.5%, oil): Assignment of $^1$HNMR for aliphatic protons are presented in Table 3.

EXAMPLE 3

Synthesis of N,N-Diethyl-O-Tosyltamoxifen (Compound VIII)

Cis- or trans- N,N-diethylhydroxytamoxifen (II) (100 mg, 0.27 mmol) was dissolved in methylene chloride (2 ml) and cooled to 0° C. Pyridine (150 μl) and tosyl chloride (55 mg, 0.27 mmol) were added. After 2 hours, the reaction mixture was diluted with methylene chloride and washed with water. The methylene chloride layer was evaporated and chromatographed on a [18]C column using 85:85:1 acetonitrile/water/triethylamine as eluant to yield cis (51 mg, 34%, oil) or trans tosyl analog (30 mg, 20%, oil): m/z 569(60, M+), 397(20, +OSO$_2$PhCH$_3$). Values for aliphatic protons are presented in Table 3.

EXAMPLE 4

Synthesis of N,N-Diethylfluorotamoxifen (Compound IV)

The present example is provided to demonstrate two methods by which compound IV may be prepared.

Method 1

Cis or trans N,N-diethylhyroxytamoxifen (II) (400 mg, 0.96 mmol) was dissolved in tetrahydrofuran (25 ml), and the solution was cooled to −40° C. A solution of triethylamine (480 μl) was added. Diethylaminosulfor trifluoride (1280 μl, 2.11 mmol) was added and the reaction mixture was stirred for three hours at −40° C. The crude material was poured into water and then extracted with ether. The ether layer was dried over anhydrous magnesium sulfate, filtered and evaporated to dryness. The mother liquor was chromatographed on a silica gel packed (3×60 cm, ACE Gloss) column using 1:1:0.1 ether/petroleum ether/triethylamine to yield purified 60 mg (15%) of trans IV (oil): Rf 0.70, and 80 mg (20%) of cis IV (oil), Rf 0.60 (1:1:0.1 ether/petroleum ether/triethylamine); trans $^1$HNMR (CDCl$_3$ δ 1.02(t, J=7.3 Hz, 6, (CH$_3$CH$_2$N), 2.57 (q, J=7.1 Hz, 4, CH$_3$CH$_2$N), 2.78(t,J=6.3 Hz, 2, OCH$_2$CH$_2$N), 2.91 (dt, J=21.5 Hz, 6.3 H, 2, CH$_2$CH$_2$F), 3.90 (t, J=6.2 Hz, 2, OCH$_2$CH$_2$N), 4.33 (dt, J=47.4 Hz, 6.3 Hz, 2, CH$_2$CH$_2$F), 6.56 (d, J=8.5 Hz, 2, ArH 3,5 to OCH$_2$), 6.75 (d, J=8.7 Hz, 2, ArH 2,6 to OCH$_2$), 7.12–7.37 (m, 10, ArH); m/z 417(50,M+)Hz. Anal. (C$_{28}$H$_{32}$NOF.$\frac{1}{2}$H$_2$O) C, H, N. Calc., C:79.40.H:7.70, N:3, 31; Found, C:79.71, H:7.61, N:3.36.cis $^1$HNMR (CDCl$_3$)δ 1.08 (T, J=7.1 Hz, 6, CH$_3$CH$_2$N), 2.64 (q, J=7.3 Hz, 4, CH$_3$CH$_2$N), 2.89–2.96 (m, 4, OCH$_2$CH$_2$N and CH$_2$CH$_2$F), 4.06 (t, J=6.4 Hz, 2 OCH$_2$CH$_2$F), 4.35(dt, J=47.1 Hz, 6.4 Hz, 2, CH$_2$CH$_2$F), 6.89–7.26 (m, 14, ArH); m/z 417 (70, M+), 402 (30). m.p. 55°–57° C. Anal. (C$_{28}$H$_{32}$NOF.0.5 H$_2$O) C,H,M, calc., C:78.84, H:7.80, N:3.28; Found, C:78.71, H:7.48, N:3.20

Method 2

N,N-Diethyl tosyl analogue of tamoxifen (VIII) (40 mg, 0.07 mmol) was dissolved in tetrahydrofuran (200 μl) and then treated with tetrabutylammonium fluoride (170 μl, 1M in tetrahydrofuran). Fifteen minutes after adding TBAF, two spots were visualized by silica gel TLC (4:1 chloroform/methanol). Both products were isolated from a silica gel Sep-Pak by elution with ether/petroleum ether/triethylamine (1:1:0.1). One product isolated was the trans isomer of compound (IV) (11 mg, 40%) and the other was a butadien derivative (30%, oil). Butadiene derivative HNMR (CDCl$_3$) δ 1.08 (t, J=7.0 Hz, 6, CH$_3$CH$_2$N), 2.65 (q, J=7.0 Hz, 4, CH$_3$CH$_2$N), 2.90 (t, J=6.0 Hz, 2, OCH$_2$CH$_2$N), 4.08 (t, J=6.0Hz, 2, OCH$_2$CH$_2$N), 4.94 (d, J=17.2 Hz, 1m CH=CH$_2$), 5.17 (d, J=10.9 Hz, 1, CH=CH$_2$), 6.78–7.26 (m, 9, ArH and CH=CH$_2$). m/z 397 (60, M+). Anal. (C$_{28}$H$_{31}$NO·1.5 H$_2$O) C,H,N. Calc., C:79.21, H:8.06: N:3.30; Found, C: 79.76, H:7.56, N:3.09.

EXAMPLE 5

Synthesis of Hydroxymethyl-N,N-Diethyl Tamoxifen (Compound III)

Clomiphene (3.8 g, 9.3 mmol) was dissolved in tetrahydrofuran (50 ml), cooled to $-40°$ C. and then treated with t-butyl lithium (1M in pentane, 20 mmol). After 10 minutes, trimethylene oxide (6 ml, 93 mmol) was added, the mixture stirred for 16 hours at room temperature, and then poured into water. The product was extracted with ether and chromatographed on a silica gel column using 1:1:0.1 ether/petroleum ether/triethylamine as eluant to yield purified trans-product (1 g, 25%), m.p. 93°-95° C. and cis- product (N,N-diethylhydroxymethyl tamoxifen) (1.0 g, 25%), m.p. 85°-87° C. Anal. ($C_{29}H_{35}NO_2$)C,H,N. Calc., C:81.08, H:8.21, N:3.26; Found, C:80.56, H:7.94, N:3.32. Values for aliphatic protons are presented in Table 3.

EXAMPLE 6

Synthesis of Cis-Tosylmethyl-N,N-Diethyltamoxifen (Compound IX)

(cis) Hydroxymethyl-N,N-diethyl tamoxifen (500 mg, 1.17 mmol) (III) was dissolved in methylene chloride (20 ml), and the solution cooled to 0° C. Pyridine (0.66 ml) and tosyl chloride (266 mg, 1.40 mmol) Were added. After 4 hours, the reaction mixture was diluted with additional methylene chloride (20 ml) and washed with water, dried over magnesium sulfate, filtered, and evaporated to yield 476 mg. The crude mixture was chromatographed on a $^{18}C$ reverse phase column using 85:15:1 acetonitrile/water/triethylamine as eluant to yield the purified cis- tosyl analogue of IX (200 mg, 29%, oil) $R_f$ 0.35 (silica gel plates, ether/petroleum ether/triethylamine 1:1:0.1), m/z 583(10, M+). Values for aliphatic protons are presented in Table 3.

EXAMPLE 7

Synthesis of Fluoromethyl-N,N-Diethyl Tamoxifen (Compound VI)

The cis- or trans-tosyl analogue of IX (117 mg, 0.2 mmol) was dissolved in tetrahydrofuran (400 µl ) according to our reported procedure.[9] Tetrabutylammonium fluoride (485 µl, 1M in tetrahydrofuran) was added, and the reaction was warmed to 80° C. After 30 minutes, the reaction was completed. The mixture was then hydrolyzed with 6N HCl 6.2 ml for 10 min. The product was chromatographed on a silica gel column, which was eluted with 1:1:0.1 ether/petroleum ether/triethylamine to yield 52 mg (60%, oil) of purified cis fluoro product (VI) or 40 mg (46% oil) of trans product $R_f$ 0.80 (silica gel plates, ether/petroleum ether/triethylamine 1:1:01), m/z 431(40, M+). Anal. ($C_{29}H_{34}NOF$) C,H,N. Calc., C:80.71, H:7.94, N:3.25; Found, C:80.39, H:8.02, N:3.13 (cis) or C:79.58, H:8.01, N:3.20 $^1$HNMR AND $^{13}$C-NMR data are shown in Table 4.

EXAMPLE 8

Preparation of N,N-Diethyliodomethyltamoxifen (X)

Tosyl analog of tamoxifen (117 mg. 0.2 mmol) was dissolved in acetone (15 ml). Sodim iodide (150 mg, 1.0 mmol) was added, the reaction was refluxed for 6h. The mixture was evaporated to dryness and chromatographed on a silica gel column using ether/petroleum ether/triethylamine (1:1:15%) eluant to yield Cis 75 mg (70%) $R_f$0.50; or trans 54 mg (50%), $R_f$0.65 (1% triethylamine in ether/petroleum ether; 1:1). m/z 539 (M+, 100), 524(20), 312(30), 191(30), 100(60), 86(100). trans m/z 539 (M+, 100), 524(30), 452(20), 191(30), 100(60), 86(100). the $^1$HNMR and $^{13}$CNMR assignments were shown in Table 5.

The end produce N,N-Diethyliodomethyltamoxifen will then be radiolabeled with $^{131}$I, as described in Example 9.

TABLE 5

$^{13}$C (50 MHz) and $^1$H (200 MHz) NMR Assignments for N,N-Diethyliodomethyltamoxifen (X) in CDcl$_3$

| Atom | $^1H(\pm 0.002$ ppm) Trans | Cis | No. of protons Trans | Cis | $^1$H (multiplicity) JHH (Hz) Trans | Cis | No. of Carbons | $^{13}$C (ppm) JHH (Hz) Trans | Cis |
|---|---|---|---|---|---|---|---|---|---|
| ar | 7.40 | 7.20 | 10 | | m | m | 6 | 135–157 | 135–157 |
| a | 6.76 | 7.10 | 2 | | d(8.8) | m | 1 | 113.37 | 114.3 |
| b | 6.54 | 7.00 | 2 | | d(8.8) | m | 1 | 113.37 | 114.3 |
| 5 | 3.90 | 4.06 | 2 | | t(6.4) | t(6.4) | 1 | 66.16 | 66.64 |
| 4 | 3.02 | 3.04 | 2 | | t(7.1) | t(7.0) | 1 | 51.59 | 51.85 |
| 3 | 2.78 | 2.88 | 2 | | t(6.4) | t(6.4) | 1 | 6.38 | 6.19 |
| 6 | 2.50 | — 2.70 | 64 | | m | m | 2 | 47.77 | 47.89 |
| 1 | 2.50 | — 2.70 | 2 | | m | m | 1 | 37.05 | 37.06 |
| 2 | 1.86 | 1.86 | 2 | | pent(7.4) | pent(7.4) | 1 | 32.92 | 32.95 |
| 7 | 1.02 | 1.02 | 6 | | t(7.1) | t(7.1) | 2 | 11.77 | 11.95 |

EXAMPLE 9

Radiosynthesis of [$^{13}$F] Fluoromethyl and [$^{131}$I] Iodomethyltamoxifen

[$^{18}$F]fluoride was produced at the University of Texas Health Science Center, Cyclotron Facility, y proton irradiation of [$^{18}$O] water (99.4% isotopic enrichment, ISOTEC INC., Miamisburg, Ohio) in a small volume silver target. Aliquots containing 50–60 mCi of $^{18}$F activity were combined with kryptofix-2,2,2 (26 mg) and potassium carbonate (4.6 mg) and dried in a vacutainer tube by azeotropic distillation with dry acetonitrile. The remaining kryptofix/[$^{18}$F]fluoride was resolubilized in acetonitrile (3 ml).

In a typical experiment,[9][$^{18}$F]fluoride (3 mCi, 200 µl) was transferred to a reaction vessel with the tosylmethyl analog of tamoxifen (IX) 1 mg). The vessel was sealed and warmed at 100° C. for 20 minutes, treated with 6 N HCl (200 µl), heated for an additional 10 min, and then spotted on a silica gel coated TLC plate for separation (ether/petroleum ether/triethylamine; 1/1/10% or chloroform/methanol; 9/1).

Authentic non-labeled fluorotamoxifen was used to confirm the presence of F-18 labeled compound. The TLC plate was cut into 0.5 cm zones for counting the activity. Using a Davidson multichannel analyzer fitted with a well type NaI crystal with appropriate shielding.

The radiochemical yield was determined as 60%. The reaction mixture was passed through a silica Sep-Pak eluted with 10% triethylamine in ether/petroleum ether (1/1). The radiochemical purity was examined using HPLC (C-18 Radial-Pak column, 8×100 mm, 1% triethylamine in acetonitrile/water (85/15) flowrate of 1.5 ml/min). The retention time of VI was 5.60 min. Radiochemical purity was >99%. A typical batch had a specific activity of approximately 2-4 Ci/μmol.

for a typical $^{131}$I displacement experiment, Na$^{131}$I (1mCi) was added to a vial containing tosylmethyltamoxifen (IX)(2 mg) in acetone. The reaction was heated at 100° C. for 30 min. and 6 N HCl was added. After 20 min. the vial was cooled and the reaction mixture was chromatographed on a silica-gel Sep-Pak column eluted with 1% triethylamine in ether:petroleum ether (1:1). The purity of the [131-I] labeled tamoxifen analog was asseses by HPLC and compared to authentic compound. The retention time for Compound X was 22 min. (Acetonitril:water:triethylamine)(85:15:1).

EXAMPLE 10

In Vitro Estrogen Receptor Binding Assay the present experiment was run to demonstrate the ability of the described fluorotamoxifen derivatives to bind estrogen receptors in vitro, and to therefrom predict the suitability of employing these tamoxifen derivatives in breast tissue for diagnostic in vivo techniques.

The relative binding affinity of the tamoxifen derivatives synthesized in Examples 1-8 and of native tamoxifen (Compound I) to estrogen receptor was determined with modification of the reported procedure.[10,11] In our procedure, we used TEA buffer for tissue preparation.

Briefly, uteri obtained from immature domestic swine (25-30 kg). Between 100 and 150 grams of the uterine tissue was homogenized in Tris buffer (10 mM, pH 7.4) (1 uterus/2 ml), which contained EDTA (1.5 mM) and sodium azide (3 mM). The homogenate was centrifuged at 100,000 g for 1 hour at 4° C. Uteri cytosol was then pretreated with dextran-coated charcoal as described.[10]

To investigate the nature of the interaction of estradiol with the estrogen receptor site, a saturation curve was obtained for [$^3$H] estradiol (10$^{-10}$ M) in the presence or absence of excess estradiol (2×10$^{-5}$ M). Uteri cytosol was incubated at 4° C. for 2 h with [$^3$H]estradiol (5 nM/tube) and competitor (ranging from 1×10$^{-4}$ M to 10$^{-5}$ M) or with estradiol (10$^{-5}$ M) (non-specific). The concentration of test compounds which decreased 50% (IC$_{50}$) of specific radioligand binding and the inhibition constant were determined.[9] Protein concentrations were determined according to the method of Lowry et al.[12]

For [$^3$H]estradiol binding, Scatchard analysis indicated a single class of binding sites with a mean Kd of 5 nM (n=9) and a mean Bmax of 376 fmol/mg protein with a Hill coefficient of 0.982. The inhibition constants (Ki) of the ligands for the estrogen receptor binding in pig uteri were then determined. The IC$_{50}$ of the ligands for the estrogen receptor was determined in vitro by their ability to displace [$^3$H] estradiol (5 nM) binding in pig uteri. These results are summarized in Table I. Fluorotamoxifen (I) binds to the estrogen receptor with high affinity as tamoxifen (K$_i$=1500 nM) (Table I). The affinity of the trans-isomer of N,N-diethylfluorotamoxifen (IV) for the estrogen receptor is two and a half times that of tamoxifen. In addition, the trans-isomer has a higher binding affinity than the cis-isomer. Increasing the side chain with one carbon resulted in the formation of fluorinated compound (VI), which showed a 6-fold (cis) and 30-fold (trans) higher affinity for the estradiol binding site than tamoxifen. The iodinated compound (X) showed 10-15 fold higher estrogen receptor affinity than tamoxifen.

TABLE 1

STRUCTURES AND RELATIVE BINDING AFFINITIES OF TAMOXIFEN DERIVATIVES

| Compound | R | X | RBA* | IC$_{50}$ (M) | K$_i$ (nM) |
|---|---|---|---|---|---|
| I (Tamoxifen) | CH$_3$ | H | 100 | 3 × 10$^{-5}$ | 15,000 |
| II | C$_2$H$_5$ | OH | | | |
| III (Cis) | C$_2$H$_5$ | CH$_2$OH | 300 | 1 × 10$^{-5}$ | |
| (trans) | | | 400 | 7 × 10$^{-6}$ | |
| IV (Cis) | C$_2$H$_5$ | F | 100 | 3 × 10$^{-5}$ | 15000 |
| (trans) | | | 250 | 1.2 × 10$^{-5}$ | 6000 |
| V | CH$_3$ | OH | | | |
| VI (Cis) | C$_2$H$_5$ | CH$_2$F | 500 | 1 × 10$^{-7}$ | 67 |
| (trans) | | | | | |
| VII (trans) | CH$_3$ | F | 100 | 5 × 10$^{-7}$ | 333 |
| VIII | C$_2$H$_5$ | O-tosyl | | | |
| IX | C$_2$H$_5$ | CH$_2$O-tosyl | | | |
| X (Cis) | C$_2$H$_5$ | CH$_2$I | 1000 | 3 × 10$^{-6}$ | 1,500 |
| (trans) | | | 1,500 | 2 × 10$^{-6}$ | 100 |
| Estradiol | | | 15,000 | 2 × 10$^{-7}$ | 100 |

*The relative binding affinity (RBA) for the pig uteri estrogen receptor is the ratio between the concentration of unlabeled tamoxifen and the competitor (× 100%) required to decrease the amount of bound [$^3$H] estradiol by 50%. Incubation was done at 4° C. The data was reproduced in triplicate. The protein concentration was determined to be 1 mg per tube.

EXAMPLE 11

In Vitro Breast Tumor Cell Assay

The present example is presented to demonstrate the applicability of the claimed fluorotamoxifen derivatives as an anti-cancer agent in humans for the treatment of estrogen-receptor positive tumors, particularly those tumors associated with human breast cancer. Additionally, an object of this experiment was to establish the potential of using the described radiolabeled fluorotamoxifen derivatives as PET agents for imaging estrogen receptors in vivo. Such agents may predict the efficiency of tamoxifen therapy for breast tumors. Aliphatic fluorination of tamoxifen was chosen based on the development of the specifically described chemical methods herein (See FIG. 1-3 step protocol) and because of the superior high specific activity observed with the described radiosynthesis method (Example 8).

The MCF7 cell line is a human tumor cell line. This cell line was cultured in MEM (Earles) medial in a 5% CO$^2$ atmosphere with 10% fetal calf serum that had been washed twice with dextran coated charcoal to reduce endogenous estrogen levels. The media was supplemented with 1 mM sodium pyruvate and 100 μm non-essential amino acids. The cell like was screened routinely for mycoplasma contamination using the Gen- Probe kit (Fisher). Cells were trypsinized and plated at a density of 5,000 cells/well in a 96 well microtiter plates and allowed to attach and recover for 24 hours.

The media was removed by aspiration and replaced with filter sterilized drug (concentration from $10^{-4}$M to $10^{-5}$M) in media. The cells were incubated for 72 hours and then stained using the mTT tetrazolium dye assay of Mosmann[13] except that after the media was removed, the blue formazan product was solubilized in 50 μl/well DMSO. Plates were shaken for 1 minute and read on a Dynatech MR600 microplate reader within an hour at a transmission wavelength of 570 nm and reference wavelength of 630 nm.

Compound VII (fluorotamoxifen), II (N,N-diethlhydroxytramoxifen, VIII (N,N-diethyl-O-tosyltamoxifen), IV (N,N-diethylfluorotamoxifen, III (diethylhydroxymethyltamoxifen), IX (N,N-diethyl-O-tosylmethyl tamoxifen), and VI (N,N-diethylfluoromehtyltamoxifen) were prepared substantially as described in Examples 1-7.

The results of the 72 hour exposure of MCF7 tumor cell line to tamoxifen or analogs are summarized in Table 2. Cis, N,N-diethylfluoromethyl tamoxifen was 3-fold more potent than tamoxifen control against this tumor cell line. In addition, both cis N,N-diethyl-fluoro, fluoromethyl- and iodomethyl isomers appear to be more potent than the trans isomers.

These results demonstrate that the described fluorotamoxifen derivatives, particularly compounds IV (cis), VI (cis and trans) and X(cis and trans) are effective as inhibiting a breast tumor cell line, and further support the reasonable expectation that these highly specific derivatives would be effective as an anti-cancer agent in treating human breast cancer.

In summary, this study demonstrates that halogenated tamoxifens with the halogen atom placed on the aliphatic chain bind to estrogen receptors in vitro and can be labeled with $^{18}$F and $^{131}$I, thus reflecting a potential for use in imaging estrogen receptors by PET and SPECT. Also, the data obtained from in vitro receptor assays suggested that the disclosed fluoroamoxifen derivatives, particularly fluoromethyl-N,N-diethyltamoxifen and iodomethyl-N,N-diethyltamoxifen, may be a potential ligand for mapping the estrogen receptor by PET and SPECT.

TABLE 2

| | \[1\]H NMR DATA OF TAMOXIFEN DERIVATIVES | | | | | | | |
|---|---|---|---|---|---|---|---|---|
| | H-1 | $J_{1,2}$ | $J_{1,2}$ | H-2 | H-3 | $J_{3,4}$ | $J_{3,4}$ | H-4 |
| II (Cis) | | 2.79 | 6.3 | 6.3 | 3.96 | 2.70 | 7.1 | 7.1 | 3.49 |
| II (trans) | | 2.72 | 6.2 | 6.3 | 3.88 | 2.76 | 7.1 | 7.1 | 3.54 |
| III (Cis) | ≈2.48 | — | 6.3 | 3.99 | ≈2.64 | — | 7.3 | 1.56 | — |
| III (trans) | ≈2.45 | — | 6.4 | 3.90 | 2.77 | 6.4 | 7.3 | 1.59 |
| VIII (Cis) | | 2.91 | 6.3 | 7.1 | 3.94 | 2.84 | 7.1 | 6.3 | 4.07 |
| VIII (trans) | ≈2.80 | — | — | ≈3.89 | ≈2.76 | — | — | ≈3.94 |
| IX (Cis) | 2.48 | 6.0 | 6.3 | 3.90 | 2.90 | 6.0 | 7.1 | 1.66 | — |

EXAMPLE 12

H-NMR and 13$_c$-NMR Assignment of Fluorotamoxifen Derivatives \[1\]HNMR Assignment \[1\]HNMR Assignment Assignment of \[1\]H-NMR for compound VI and X was done by two dimensional NMR which includes COSY, Long Range COSY and HC COSY, Long Range HC COSY (COSY Homonuclear Chemical Shift Correlation). The aromatic portion is subdivided into three isolated spin systems at 200 MHz. In the trans isomer, two spin systems were readily established for aromatic protons a and b (Shanni, 1985; McCague, 1988). For compound VI, a correlation among the H1 methylene protons (resonates at 2.76 ppm for cis and 2.55 ppm for trans), the H2 geminal methylene protons (resonates at 1.79 ppm for cis and 1.80 ppm for trans) and H3 protons (resonates at 4.38 ppm for cis and 4.42 ppm for trans) was observed during the analysis of the COSY Spectrum as shown in Table 4. In addition, the protons at the 4 and 5 -ethylene bridge correlated with each other using the COSY spectrum analysis. H-5 resonates down field at 3.99 ppm (cis) and 3.91 ppm (trans) whereas H-4 resonates at 2.8 ppm (cis) and 2.79 ppm (trans). H-6 protons of the ethyl group showed a gradruplet (resonates at 2.57 ppm for cis and 2.57 ppm for trans) which directly correlates with H-7 methyl protons at 1.01 ppm (cis) and 1.03 ppm (trans). The \[1\]HNMR data are shown at Table 4.

13C-NMR Assignment

Proton resonance assignments were unequivocally assigned by COSY spectrum. Protonated carbon resonance was assigned from HC-COSY spectrum. The chemical shift for cis and trans isomers of compound VI is shown in Table 4 and for compound X is shown in Table 5.

TABLE 3

| | \[1\]H NMR DATA OF TAMOXIFEN DERIVATIVES (Carbon number shown of supra) | | | | | | | |
|---|---|---|---|---|---|---|---|---|
| | H-1 | $J_{1,2}$ | $J_{1,2}$ | H-2 | H-3 | $J_{3,4}$ | $J_{3,4}$ | H-4 |
| II (Cis) | 2.79 | 6.3 | 6.3 | 3.96 | 2.70 | 7.1 | 7.1 | 3.49 |
| II (trans) | 2.72 | 6.2 | 6.3 | 3.88 | 2.76 | 7.1 | 7.1 | 3.54 |
| III (Cis) | ≈2.48 | — | 6.3 | 3.99 | ≈2.64 | — | 7.3 | 1.56 |
| III (trans) | ≈2.45 | — | 6.4 | 3.90 | 2.77 | 6.4 | 7.3 | 1.59 |
| VIII (Cis) | 2.91 | 6.3 | 7.1 | 3.94 | 2.84 | 7.1 | 6.3 | 4.07 |
| VIII (trans) | ≈2.80 | — | — | ≈3.89 | ≈2.76 | — | — | ≈3.94 |
| IX (Cis) | 2.48 | 6.0 | 6.3 | 3.90 | 2.90 | 6.0 | 7.1 | 1.66 |

TABLE 4

$^{13}$C (50 MHz) and $^1$H (200 MHz) NMR ASSIGNMENTS FOR N,N-DIETHYLFLUOROMETHYLTAMOXIFEN (X) in CDCL$_3$

| Atom | $^1$H (±0.02 ppm) Trans | $^1$H (±0.02 ppm) Cis | No. of protons Trans/Cis | $^1$H (multiplicity) $J_{HH}$(Hz) Trans | $^1$H (multiplicity) $J_{HH}$(Hz) Cis | No. of carbons | $^{13}$C (ppm) $J_{HH}$(Hz) Trans | $^{13}$C (ppm) $J_{HH}$(Hz) Cis |
|---|---|---|---|---|---|---|---|---|
| Ar | 7.40 | 7.20 | 10H | m | m | 6C | 135–157 | 135–157 |
|  |  |  |  |  |  | 10C | 126–131 | 126–131 |
| a | 6.76 | 7.10 | 2H | d(8.8) | m | 1C | 113.37 | 114.3 |
| b | 6.54 | 7.00 | 2H | d(8.8) | m | 1C | 113.37 | 114.3 |
| 5 | 3.90 | 4.06 | 2H | t(6.4) | t(6.4) | 1C | 66.16 | 66.64 |
| 4 | 3.02 | 3.04 | 2H | t(7.1) | t(7.0) | 1C | 51.59 | 51.85 |
| 3 | 2.78 | 2.88 | 2H | t(6.4) | t(6.4) | 1C | 6.38 | 6.19 |
| 6 | 2.50 | 2.70 | 4H | m | m | 2C | 47.77 | 47.89 |
| 1 | 2.50 | 2.70 | 2H | m | m | 1C | 37.05 | 37.06 |
| 2 | 1.86 | 1.86 | 2H | pent(7.4) | pent(7.4) | 1C | 32.92 | 32.92 |
| 7 | 1.02 | 1.02 | 6H | t(7.1) | t(7.1) | 2C | 11.77 | 11.95 |

PROPHETIC EXAMPLE 13

Proposed In Vivo Imaging of Pig Uterus and Ovaries with [F-18] Fluromethyltamoxifen The present prophatic example is proposed to establish the potential utility of the claimed tamoxifen derivatives in the imaging of estrogen receptor rich tissues such as the uterus and ovaries.

In this study, 10 female immature pigs (30 Kg/pig) will be sedated with ketamine hydrochloride (30 mg/kg, i.m.). Each pig will then be intubated and placed on inhalation anesthesia consisting of halothane (1.5%0, nitrous oxide (0.3 1/min) and oxygen (0.8 l /min). The animals were then broken up into two groups of 5 pigs each, designated Group 1 and Group 2. Group 1 animals were unblocked (i.e., did not receive an estrogen receptor blocking agent). Group 2 animals were blocked (i.e., received an estrogen receptor blocking agent, estradiol; dose=5 g/pig). All animals were injected with the [F-18] fluoromethyl tamoxifen (dose=2 mCi/pig; i.u.). The total volume of [F-18] FMTX injected will be a 1 ml volume in a 10% ethanol-saline solution. All intravenous injections will be into the ear vein.

30 minutes after injection with [F-18]-FMTX or [F-18]-FMTX +estradiol, a PET scan of the liver and pelvic area will be performed for about 120 minutes (2 hours). After the PET scans have been performed, all animals will be killed by an overdose of sodium pentobarbital (60 mg/kg) by intravenous injection.

The PET scans will then be examined to assess specificity of the [F-18]-FMTX binding to estrogen receptors. The "unblocked" tissue scans will be run as controls and compared to an unblocked tissue scan to establish that the radiolabeled tamoxifen is actually binding specifically the estrogen receptors in the tissue.

This study is being performed in order to establish the applicability of using the described [F-18]-FMTX derivatives in vivo and to demonstrate that the high specific affinity of the described radiolabeled tamoxifen derivatives injected in vivo specifically for estrogen-receptor rich tissues.

PROPHETIC EXAMPLE 14

In Vivo Tissue Distribution of [F-18] FMTX in Estrogen-Primed Immature Rats

The present prophetic example is provided to demonstrate the tissue specificity of the described [F-18]-FMTX derivatives for tissues n vivo and the potential use of such highly tissue-selective derivatives in the analysis of human tissues. The establishment of a "focused" tissue concentration of a radiolabeled estrogen receptor ligand will provide the advantage of requiring minimal patient radioisotope exposure.

20 female Sprague-Dawley immature rats (80 g/rat) will be primed with estradiol (5 ug/day/rat in 0.1 ml of 5% estranol-sunflower oil, 1:p.) for three consecutive days. The estrogen primed rats will then be divided into three groups, Group 1(5 rats), Group 2 (10 rats) and Group 3 (5 rats). Each group will be treated according to the following schedule:

|  | n | [F-18] FMTX | Estradiol |
|---|---|---|---|
| Group 1 | 5 | 20 µCi | 0 |
| Group 2 | 10 | 200 µCi | 0 |
| Group 3 | 5 | 200 µCi | 60 µg/rat |

The total volume of [F-18] FMTX injected will be a 0.1 ml volume in a 10% ethanol-saline solution.

One hour after the above treatments, all animals in Group 1, 5 of the animals in Group 2, and all of the animals in Group 3 will be sacrificed. The remaining 5 animals in Group 2 are to be sacrificed 3 hours after the above treatments.

The following organs will be excised from each animal. The percent injected dose (PID)/gm tissue +SD(n=5) will then be determined. In order to determine receptor-mediated uptake in the uterus, uterus/muscle (non-target tissue) and uterus/blood ratio will be calculated.

| Tissues to be Examined | | |
|---|---|---|
| uterus | muscle | brain |
| ovaries | lung | liver |
| blood | heart | kidney |
| bone | fat | |

The information to be collected in the example will provide accurate measure of the target/non-target tissue specificity of the described radiolabeled tamoxifen derivatives. The tissue/muscle ratio of the distributed radiolabeled tamoxifen derivative is projected to be 5/10. The target tissue/background ratio will also be determined. The biodistribution of radiolabeled tamoxifen in the blood of the animal(s) being treated will also be determined. These determinations will establish the specificity of the tamoxifen derivatives for targeted tissues as well as the whole body biodistribution of the derivatives when used in vivo.

PROPHETIC EXAMPLE 15

Proposed In Vivo Tissue Uptake of Cis or Trans [$^{131}$I] Iodomethytomoxifen

This example is proposed in order to establish if there exists any tissue uptake differences between the cis- and transform of the [$^{131}$I] Iodomethyltamoxifen (*IMTX) derivative.

Iodomethyltamoxifen will be prepared as described in Example 9.

50 immature female Sprague-Dawley Rats (21-25 days, 65 gleach) will be used in this proposed experiment. Half of the rats (25 animals) will be treated with cis-*IMTX, and the remaining half of the animals (25 animals) will be treated with trans-*IMTX. The *IMTX will be formulated in ethanol:water (1:9) at about 50 μCi/ml. Each of the two groups of *IMTX-pretreated animals will then be divided into 3 subgroups and administered the following schedule of drugs:

| Group 1 (cis *IMTX) | A | 15 | 5 μCi | 0 | 0 | — |
|---|---|---|---|---|---|---|
| | B | 5 | 0 | 5 μg | 0 | 5 μCi(cis) |
| | C | 5 | 0 | 0 | 100 μg | 5 μCI(cis |
| Group 2 (trans *IMTX) | A | 15 | 15 μCi | | 0 | 0 — |
| | B | 5 | 0 | 5 μg | 0 | 5 μCi (trans) |
| | C | 5 | 0 | 0 | 100 μg | 5 μCi (trans) |

Estradiol will be formulated in ethanol/water (1:9) and injected S. C. tamoxifen will also be formulated in ethanol/water (9:1) and injected S. C. The total volume injected of each treatment will be 0.1 ml.

Groups 1B and 1C and Groups 2B and 2C will then be injected a second time (after a 30-minute incubation period) with 5μCi of either cis⁻or trans⁻*IMTX. Group 1A (N=15) and Group 2A (n-15) will again be subdivided into 3 groups of 5 rats each, and sub-groups of 5 animals sacrificed at 2 hour, 4 hour and 24 hour intervals, according to the following table.

| | | | n | Sacrifice |
|---|---|---|---|---|
| Group 1 (cis) | A | 1' | 5 | 2 hr |
| | | 2' | 5 | 4 hr |
| | | 3' | 5 | 24 hr |
| Group 2 (trans) | B | 1' | 5 | 2 hr |
| | | 2' | 5 | 4 hr |
| | | 3' | 5 | 24 hr |

Each rat will be sacrificed at the designated interval using ($O_2$) euthanasia and particular tissues will be removed. The following tissues will then be dissected out of each animal, weighed, and counted on a gamma counter.

| Bad Tissues to be Dissected | | |
|---|---|---|
| Heart | Kidneys | Uterus |
| Liver | Muscle | Blood (1 ml) |
| Lungs | Ovaries | |

The radioactivities of each organ will then be calculated as the percent of injected dose times the weight in Kilograms per gram of tissue. Specific estrogen receptor binding will be calculated at the concentration of activity in the tissue of the group without pretreatment minus the pretreatment group.

METHYL PROPHETIC EXAMPLE 16

Proposed Human use of Fluoro Tamoxifen and Iodomethyltamoxifen in Imaging of Estrogen Receptor Positive Tumors The present experiment is provided to demonstrate the applicability of the present invention in imaging estrogen-receptor positive tumor cells (cancer) in humans. More specifically, the present prophetic example is aimed at outlining a method by which the described fluorotamoxifen molecules may be used to image estrogen receptor positive tumors in vivo, most particularly those which typically occur in breast tissue.

In a most preferred embodiment of the proposed method, the halogenated tamoxifen derivative, trans-fluoromethyl-N,N-diethyltamoxifen (compound VI) and trans iodomethyl-N,N-dieththyltamoxifen (compound X), is the radiopharmaceutical of choice to be used as the estrogen receptor imaging agent in a standard PET (positron emission tomography) and SPECT analysis. The procedure would be substantially the same as that outlined by Minton et al.[4] The most significant modification of this procedure, of course, is that the estradiol-based derivatives described by Minton would not be used, and instead the tamoxifen-based derivatives of the claimed invention.

Briefly stated, the claimed method for use in imaging breast tumors in a patient wherein [$^{18}$F] N,N-diethyl-fluoromethyltamoxifen or [$^{131}$I] N,N-diethyliodomethyltamoxifen is employed as the imaging agent, will comprise the following steps: administering to the patient a sufficient amount (about 10 mCi) of the fluorotamoxifen derivative to provide a treated patient. The treated patient is then to be positioned supine in the PET device, at which time an emission scan of the chest at the level of the breast mass is to be performed. Most preferably, the emission scan is to be performed for a 20 minute duration to be performed most preferably about 110 minutes after the injection. Most preferably, the tumor location is to be confirmed by palpation of the tissue after the patient is in the described supine position.

The PET images obtained are then to be evaluated for the presence or absence of focally increased uptake of the fluorotamoxifen ligand in the breasts and in the axillae as these were included in the field of view of the PET scanner. Those sites determined from the PET images to have demonstrated potential uptake is to be designated as accordingly abnormal foci uptake of the fluorotamoxifen derivative.

BIBLIOGRAPHY

1. T. Nogrady (1985), *Medicinal Chemistry: A Biochemistry Approach*, Oxford University Press, New York, pp. 210-19.
2. Robertson et al. (1982), *J. Org. Chem.*, 47:2387-93.
3. Kallio et al. (1986), *Cancer Chemother Pharmacol.*, 17:103-8.
4. Mintun et al. (1988), *Radiology*, 169:45-8.

5. Hamacher et al. (1986), *J. Nucl. Med.*, 27(2):235-8.
6. Foster et al. (1986), *Anticancer Drug Design*, 1:245-57.
7. Still et al. (1978), *J. Orn. Chem.*, 43:2923-4.
8. Foster et al. (1985), *J. Med. Chem.*, 28:1491-7.
9. Wieland et al. (1988), *Int. Rad. J. Appl. Instrum.* [A], 39:1219-25.
10. J. H. Fishman (1983), *Biochem. Biophys. Res. Commun.*, pp. 713-18.
11. McCague et al. (1988 ), *J Med. Chem.*, 31:1285-90.
12. Lowry et al. (1951), *J. Biol. Chem.*, 193:265-75.
13. U.S. Pat. No. 4,839,155—McCague (1989)
14. U.S. Pat. No. 3,288,806—Dewald (1966)
15. Allen et al. (1980), *British Journal of Pharmacology*, 71:83-91.
16. Pomper et al. (1988), *J. Med. Chem.*, 31(7):1360-63.
17. Kiesewetter et al. (1984), *J. Organ. Chem.*, 49:4900.
18. Fur et al. (1984), *Pharmac. Ther.*, 25:127.
19. Kiesewetter et al. (1984) *J. Nocl. Med.*, 25:1212-1221.
20. Hochberg, R. B. (1979) *Science*, 205:1138-1140.
21. Katzenellenbogen et al. (1981), *J. Nucl. Med.*, 22:42-97.
22. Shani et al. (1985) *J. Med. Chem.*, 28:1504-1511.
23. Hanson et al. (1982), *Int. J. Nucl. Med. Biol.*, 9:105-107.

What is claimed is:

1. A tamoxifen derivative for selectively binding estrogen receptors of a tissue which is a compound of formula (1):

wherein $R_1$ is fluoromethyl, iodomethyl, chloromethyl, bromomethyl, or hydroxymethyl.

2. The tamoxifen derivative of claim 1 wherein $R_1$ is fluoromethyl.

3. The tamoxifen derivative of claim 1 wherein $R_1$ is iodomethyl.

4. The tamoxifen derivative of claim 2 or 3, wherein the binding affinity of the tamoxifen derivative to estrogen receptors is at least thirty times greater than tamoxifen.

5. A radiolabeled tamoxifen derivative having a high specific activity for estrogen receptors in an animal which is a compound of formula (2)

wherein X is 18-F, 131-I, 18-F fluoromethyl, or 131-I iodomethyl.

6. The radiolabeled tamoxifen derivative of claim 5 wherein X is [18-F] fluoromethyl or 131-I] iodomethyl.

7. The radiolabeled tamoxifen derivative of claim 5 wherein X is 18-F fluoromethyl.

8. A method for selectively inhibiting an estrogen-receptor positive tumor in a patient comprising administering to the patient the tamoxifen derivative of claim 5 in an amount effective to inhibit the estrogen-receptor positive tumor.

9. An estrogen receptor radiopharmaceutical agent having a high specific activity for estrogen receptors of a target tissue in an animal comprising a radiolabeled tamoxifen derivative, wherein the tamoxifen derivative is substituted at a non-phenolic alkyl side chain to include an alkyl of at least two carbon atoms and wherein the radiolabel comprises $^{18}F$ or $^{131}I$ and is located at said alkyl chain.

10. The estrogen receptor radiopharmaceutical agent of claim 9, wherein the alkyl comprises a chain of three carbons.

11. The estrogen receptor radiopharmaceutical agent of claim 10, further defined as including an $^{18}F$ radiolabel and as comprising N,N-diethylfluoromethyltamoxifen or fluoromethytamoxifen.

12. The estrogen receptor radiopharmaceutical agent of claim 11, further defined as including an $^{131}I$ radiolabel and as comprising iodomethyltamoxifen.

13. A method for selectively imaging estrogen receptors in an estrogen receptor-rich target tissue of a patient comprising labeling the estrogen receptor with a radiolabeled N,N-diethyl amino fluoromethyltamoxifen derivative comprising a halogen substituted alkyl chain tamoxifen molecule labeled with 18F, said method comprising the steps of:
administering a sufficient quantity of the alkyl-substituted tamoxifen derivative labeled with 18F to the patient;
positioning the patient supine in a PET device;
performing an emission scan of the estrogen-receptor rich tissue, and obtaining a PET image of the tissue; and
evaluating the PET image for the presence or absence of focally increased uptake of the radiolabel in the estrogen-receptor rich tissue.

14. The method of claim 13 wherein the radiolabelled fluorotamoxifen derivative comprises trans- [18-F]fluoromethyl-N,N-diethyltamoxifen.

15. The method of claim 13 wherein the estrogen receptor-rich tissue is breast tissue.

16. The method of claim 13 wherein the emission scan is performed for about 20 minutes about 110 minutes after the administration of the alkyl-substituted tamoxifen derivative.

* * * * *